(12) United States Patent
Takahashi et al.

(10) Patent No.: US 7,767,148 B2
(45) Date of Patent: Aug. 3, 2010

(54) STAINING/COVERING SYSTEM

(75) Inventors: Tomio Takahashi, Chikuma (JP);
Hiroyuki Minemura, Chikuma (JP)

(73) Assignees: Sakura Seiki Co., Ltd., Nagano (JP);
Sakura Finetek Japan Co., Ltd., Tokyo (JP)

( * ) Notice: Subject to any disclaimer, the term of this patent is extended or adjusted under 35 U.S.C. 154(b) by 286 days.

(21) Appl. No.: 11/886,025

(22) PCT Filed: Mar. 7, 2006

(86) PCT No.: PCT/JP2006/304389

§ 371 (c)(1),
(2), (4) Date: Sep. 10, 2007

(87) PCT Pub. No.: WO2006/095737

PCT Pub. Date: Sep. 14, 2006

(65) Prior Publication Data

US 2008/0193333 A1    Aug. 14, 2008

(30) Foreign Application Priority Data

Mar. 11, 2005   (JP) ............................. 2005-068719

(51) Int. Cl.
*G01N 21/00* (2006.01)

(52) U.S. Cl. ............................. 422/65; 422/63; 422/64; 422/67; 422/99; 422/100; 436/180

(58) Field of Classification Search ............. 422/63–67, 422/99–100; 436/180
See application file for complete search history.

(56) References Cited

U.S. PATENT DOCUMENTS

| 5,573,727 | A | 11/1996 | Keefe et al. |
| 5,601,650 | A | 2/1997 | Goldbecker et al. |
| 7,153,474 | B2 * | 12/2006 | Thiem .......................... 422/63 |
| 2003/0047567 | A1 | 3/2003 | Plank et al. |
| 2003/0049104 | A1 * | 3/2003 | Thiem et al. ................. 414/267 |

FOREIGN PATENT DOCUMENTS

| JP | 8-500434 A | 1/1996 |
| JP | 2001-2731 A | 1/2001 |
| JP | 2001-337280 A | 12/2001 |
| JP | 2002-71538 A | 3/2002 |
| JP | 2003-149102 A | 5/2003 |
| JP | 2003-156419 A | 5/2003 |
| JP | 2005-300323 A | 10/2005 |

* cited by examiner

*Primary Examiner*—Jyoti Nagpaul
(74) *Attorney, Agent, or Firm*—Birch, Stewart, Kolasch & Birch, LLP

(57) ABSTRACT

The present invention provides a staining/covering system comprising a staining apparatus and a covering apparatus arranged in close proximity to each other, in which slide glass attached with a specimen sample stained in the staining apparatus can be transferred to the covering apparatus without using an apparatus for conveying the slide glass in the staining apparatus. The staining/covering system comprises the staining apparatus (10) for staining the specimen sample sliced and pasted to the slide glass, and the covering apparatus (12) being arranged in close proximity to the staining apparatus and covering a cover film or a cover glass onto the specimen sample of the slide glass subjected to desired staining in the staining apparatus (10), and the system is characterized in that means for transferring the slide glass having a specimen sample stained in the staining apparatus (10) from the inside of the staining apparatus to the inside of the covering apparatus is provided in the covering apparatus (12).

6 Claims, 14 Drawing Sheets

STAINING/COVERING SYSTEM

FIELD OF TECHNOLOGY

The present invention relates to a staining/covering system, more precisely relates to a staining/covering system comprising a staining apparatus for staining a specimen sample sliced and pasted to a slide glass and a covering apparatus for covering a cover film or a cover glass onto the specimen sample of the slide glass subjected to desired staining in the staining apparatus.

BACKGROUND TECHNOLOGY

In hospitals and laboratories, a specimen sample sliced from a specimen and pasted to a slide glass is desirably stained, and then a cover film or a cover glass is covered onto the specimen sample for microscopic observation. Usually, the staining process and the covering process are performed by a dedicated staining apparatus and a dedicated covering apparatus.

Conventionally, a slide glass having a specimen sample stained by a staining apparatus is manually transferred to a covering apparatus because the staining apparatus and the covering apparatus are separately installed.

To efficiently stain and cover, a full automatic staining/covering system has been required.

To realize such the system, Patent Document 1 discloses a staining/covering system comprising: a covering apparatus having a casing; a staining apparatus whose casing contacts a part of the casing of the covering apparatus; a plurality of tanks for storing staining liquid, cleaning liquid, etc.; racks (baskets) for storing slide glasses, on which specimen samples are pasted (slide glasses attached with specimen samples); a robot arm acting as means for conveying the rack between the predetermined tanks so as to stain the slide glasses attached with specimen samples by the staining apparatus, wherein the robot arm is used as means for transferring the rack, which stores the slide glasses attached with stained specimen samples, into the covering apparatus. Patent Document 1: Japanese Patent Kokai Gazette No. 2003-149102

DISCLOSURE OF THE INVENTION

In the staining/covering system disclosed in the above described Patent Document 1, the staining process and the covering process including the transferring process, in which the slide glasses attached with specimen samples are transferred from the staining apparatus to the covering apparatus, can be full-automatically performed.

In the staining apparatus having a plurality of the tanks storing staining liquids and cleaning liquid, a plurality of the racks storing the slide glasses attached with specimen samples are usually soaked in different staining liquids stored in the tanks. Therefore, a tact time of the conveying means, e.g., robot arm, which transfers the racks storing the slide glasses attached with specimen samples between the predetermined tanks, is short.

Since the conveying means in the staining apparatus, e.g., robot arm, whose tact time is short, is used as the transferring means for transferring the racks to the covering apparatus, actual timing of conveying the racks storing the slide glasses attached with specimen samples to the predetermined tank will be delayed from the desired timing, or actual timing of transferring the racks storing the slide glasses attached with stained specimen samples into the covering apparatus will be delayed from the desired timing.

To solve the problems, a high speed conveying means, e.g., high speed robot arm, must be employed so as to further shorten the tact time of the conveying means in the staining apparatus.

However, the staining apparatus equipped with the high speed conveying means is the dedicated apparatus of the staining/covering system capable of full-automatically performing a series of the staining process and the covering process. Therefore, the conventional staining apparatus equipped with the low speed conveying means cannot be employed in the staining/covering system.

The high speed conveying means is expensive, so a manufacturing cost of the staining/covering system must be high. Further, increasing the speed of the conveying means is limited.

In the staining/covering system disclosed in the above described Patent Document 1, the staining apparatus and the covering apparatus must be precisely connected so as to securely transfer the racks from the staining apparatus to the covering apparatus. However, the staining apparatus and the covering apparatus are heavy, so it is difficult to correctly position and precisely connect the both apparatuses.

An object of the present invention is to provide a staining/covering system comprising: a staining apparatus for staining a specimen sample sliced and pasted to a slide glass; and a covering apparatus being arranged in close proximity to the staining apparatus and covering a cover film or a cover glass onto the stained specimen sample of the slide glass, wherein the slide glass attached with the stained specimen sample is transferred to the covering apparatus without using a slide glass conveying unit of the staining apparatus, and wherein the staining apparatus and the covering apparatus can be easily combined.

The inventors of the present invention have studied to solve the above described problems and found that a slide glass attached with a stained specimen sample can be transferred to a covering apparatus, without using a slide glass conveyor unit of the staining apparatus, by providing means for transferring the slide glass from the staining apparatus to the covering apparatus in the covering apparatus, so that the present invention was achieved.

Namely, the staining/covering system of the present invention comprises: a staining apparatus for staining a specimen sample sliced and pasted to a slide glass; and a covering apparatus being arranged in close proximity to the staining apparatus and covering a cover film or a cover glass onto the specimen sample of the slide glass subjected to desired staining in the staining apparatus, and the system is characterized in that means for transferring the slide glass having a specimen sample stained in the staining apparatus from the inside of the staining apparatus to the inside of the covering apparatus is provided in the covering apparatus.

In case that the transferring means transfers a basket, in which the slide glass is stored, from the staining apparatus to the covering apparatus, and the staining apparatus or the covering apparatus has means for setting a mounting position in the staining apparatus, at which the basket to be transferred to the covering apparatus is mounted, to a control section for controlling means for conveying the slide glass, which is provided in the staining apparatus, or a control section for controlling the transferring means of the covering apparatus, positions of the staining apparatus and the covering apparatus can be easily adjusted. For example, even if a distance (a distance in a direction of transferring the basket) between an opening section of a casing of the covering apparatus, through which the basket enters and goes out, and an opening section of a casing of the staining apparatus is slightly different from a predetermined distance and a transferring distance of the transferring means of the covering apparatus is slightly varied, the mounting position in the staining apparatus, at which the basket to be transferred to the covering apparatus is mounted, can be easily corresponded to the transferring distance of the transferring means. Therefore, accurate positioning control of the staining apparatus and the covering apparatus can be eased, so that the both apparatuses can be easily combined.

In case that casings of the staining apparatus and the covering apparatus are arranged to partially contact each other at least, the staining/covering system can be smaller in size.

In case that, the transferring means transfers the slide glass having the specimen sample stained in the staining apparatus from the staining apparatus to the covering apparatus with the specimen sample being soaked in a protective solution, damage of the specimen sample can be avoided while transferring.

In the staining/covering system, the staining apparatus may comprise: a basket in which one or a plurality of slide glasses having specimen samples are inserted perpendicular to a bottom part; a plurality of tanks storing staining liquid or cleaning liquid, in which the basket is soaked so as to stain or clean the specimen sample or samples of the slide glass or glasses; a movable tank being reciprocally moved between the staining apparatus and the covering apparatus by the transferring means provided in the covering apparatus; and means for conveying the basket to the predetermined tank and conveying the basket, in which the slide glass or glasses having the specimen sample or samples stained or cleaned are stored, to the movable tank, which has located at a predetermined position in the staining apparatus, by the transferring means.

In the staining/covering system, the covering apparatus may comprise: a movable tank in which a basket transferred from the staining apparatus, in which one or a plurality of slide glasses having the specimen samples stained, is accommodated; means for transferring the slide glass from the movable tank to a covering position, at which the cover film or the cover glass is pasted onto the specimen sample, and transferring the slide glass, on which the cover film or the cover glass has been pasted, into the basket; means for dropping a solvent or a mounting medium onto the specimen sample on the slide glass at a mid position of the way to the covering position; and means for pressing the cover film or the cover glass onto the solvent or the mounting medium on the specimen sample so as to paste the cover film or the cover glass thereon.

In case that a protective solution for protecting the specimen sample is stored in the movable tank, damage of the specimen sample, which is accommodated in the movable tank, can be prevented while transferring.

EFFECTS OF THE INVENTION

In the staining/covering system of the present invention, the transferring means, which transfers the slide glass having the specimen sample stained in the staining apparatus from the inside of the staining apparatus to the inside of the covering apparatus, is provided in the covering apparatus.

With this structure, the slide glass can be transferred to the covering apparatus without using a slide glass conveyor unit of the staining apparatus.

Therefore, the staining/covering system can be designed without considering a tact time of the slide glass conveyor unit of the staining apparatus, and the conventional staining apparatus can be employed.

BEST MODE FOR CARRYING OUT THE INVENTION

Figure 1:
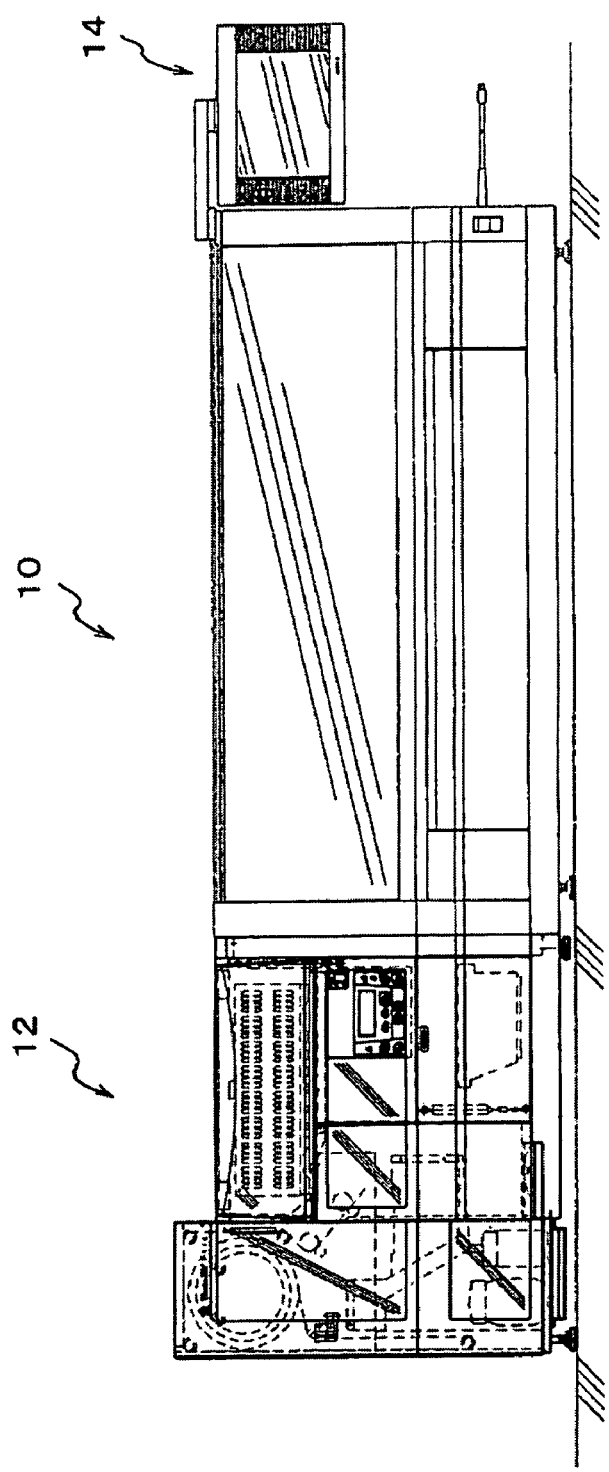
FIG. 1 is a front view of an embodiment of the staining/covering system of the present invention.

An example of a staining/covering system of the present invention is shown in FIG. 1. As shown in FIG. 1, casings of a staining apparatus 10 having a monitor 14 and a covering apparatus 12 are arranged to contact each other.

Figure 2:
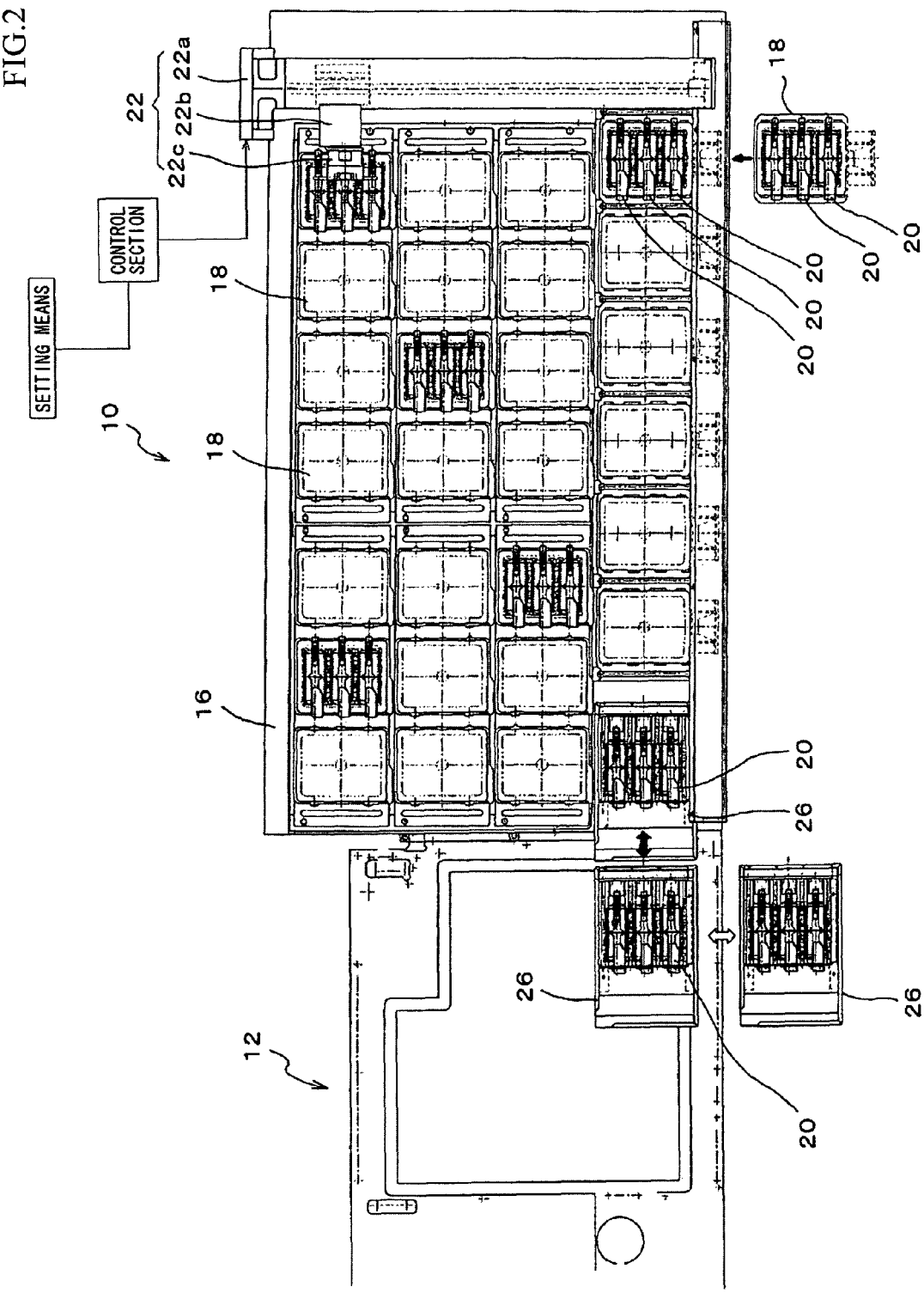
FIG. 2 is a partial plan view of a staining apparatus 10 of the staining/covering system shown in FIG. 1.

As shown in a plan view of FIG. 2, tanks 18, 18 . . . , in which various kinds of staining liquids and cleaning liquids are stored, are provided in a rectangular tank storage section 16 of the staining apparatus 10, and three baskets 20, 20 and 20, each of which stores a plurality of slide glasses attached with specimen samples, are accommodated in each of the tanks 18.

To stain specimen samples, they are usually soaked in a plurality of kinds of staining liquids and cleaning liquids. Therefore, the staining liquids and the cleaning liquids for staining the specimen samples are stored in the tanks 18, 18 . . . , and the basket 20 is inserted into the tank 18 storing the prescribed staining liquid or the cleaning liquid so as to soak the specimen samples on the slide glasses in the staining liquid or the cleaning liquid for a prescribed time period. Next, the soaked basket 20 is lifted upward from the tank 18 and conveyed to and soaked into the next tank 18 storing another staining liquid or the cleaning liquid.

The baskets 20 are conveyed by basket conveying means 22. The basket conveying means 22 is constituted by: a transversal member 22a being spanned parallel with a narrow edge of the rectangular tank storage section 16 and capable of moving along a long edge thereof; a vertical member 22b being arranged perpendicular to the transversal member 22a and capable of moving along the transversal member 22a; and an elevating member 22c being capable of vertically moving along the vertical member 22b.

Figure 3:
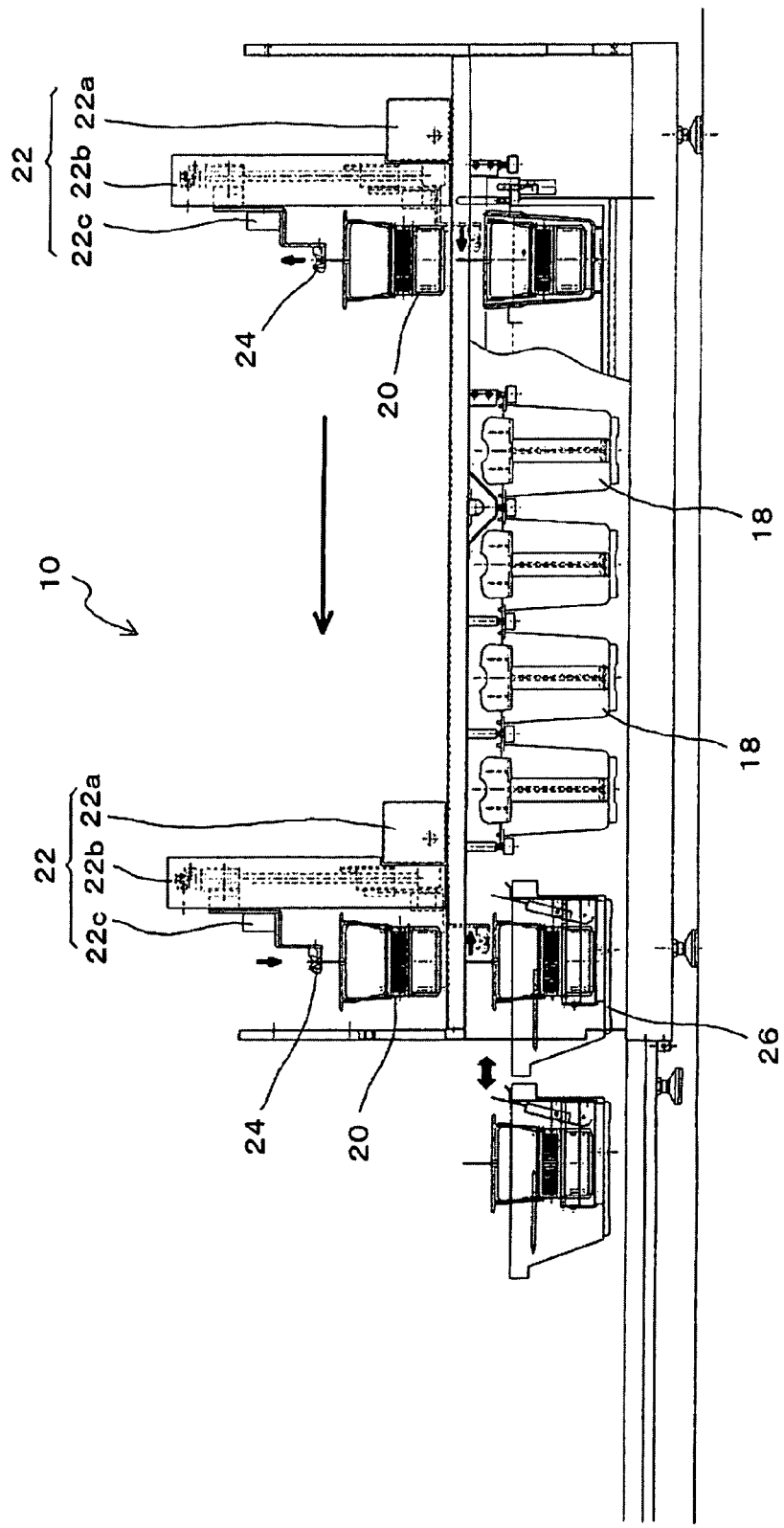
FIG. 3 is a partial side sectional view of basket conveying means 22 of the staining apparatus 10 shown in FIG. 2, wherein action of the means is explained.

As shown in FIG. 3 which is a partial side sectional view of the staining apparatus, the elevating member 22c has a holder 24. The holder 24 holding the basket 20 is vertically moved together with the elevating member 22c, moved along the transversal member 22a together with the vertical member 22b and moved along the long edge of the rectangular tank storage section 16 together with the transversal member 22a.

Figure 4A:
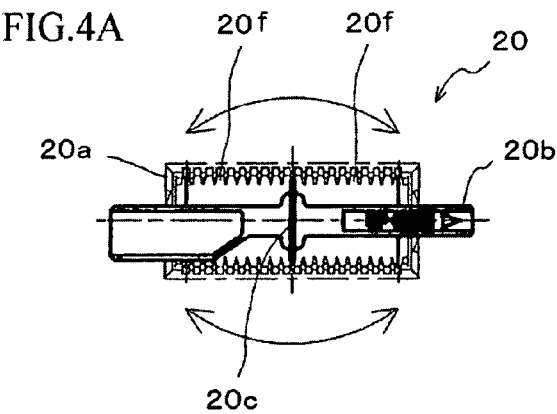
FIGS. 4A-4C are a plan view, a front view and a side view of a basket 20 used in the staining apparatus 10 and a covering apparatus 12.
Figure 4C:
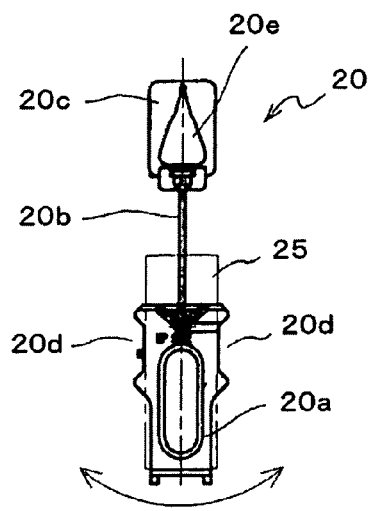
Figure 4B:
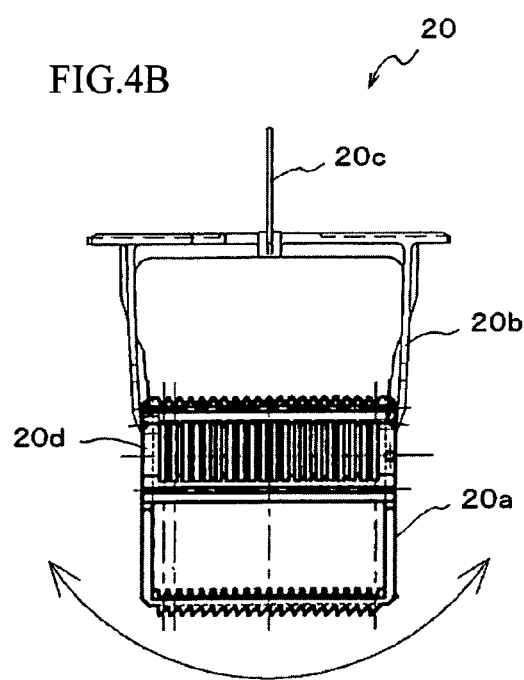

As shown in FIGS. 4B and 4C, the basket 20 is constituted by: a main body part 20a having side faces, in which grooves 20d and 20d are respectively formed; a handle 20b being rotatably attached to the main body part 20a so as to suspend the main body part 20a; and a basket hook 20c being provided to the handle 20b. A hole 20e for engaging with the holder 24 of the basket conveying means 22 is bored in the basket hook 20c (see FIG. 4C).

As shown in FIG. 4A, guide grooves 20f, 20f . . . , whose widths are equal to a width of the slide glass to be stored, are formed in inner faces of side walls of the main body part 20a, and the slide glasses are, as shown in FIG. 4A, inserted therein and arranged perpendicular or near-perpendicular to a bottom part of the main body part 20a.

The hole 20e of the basket hook 20c of the basket 20 shown in FIG. 4 is engaged with the holder 24 of the basket conveying means 22, so the basket 20 is swung in directions of arrows shown in FIGS. 4A-4C when the basket 20 is moved. By swinging the basket 20, the staining liquid, etc. stuck on the basket 20 are spattered and mixed with other staining liquids, etc., and the basket 20 located above the tank 18 contacts the edge of the tank 18 and is damaged.

Figure 5:
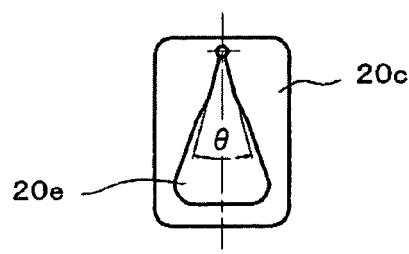
FIG. 5 is a front view of a basket hook 20c provided to a handle of the basket 20 shown in FIG. 4.

Thus, the basket hook 20c having the hole 20e shown in FIG. 5 and the holder 24 shown in FIG. 6 are employed so as to minimize the swing of the basket 20 while the basket conveying means 22 conveys the basket 20.

The basket hook 20c shown in FIG. 5 has the triangular hole 20e, which can be engaged with the holder 24.

Figure 6A:
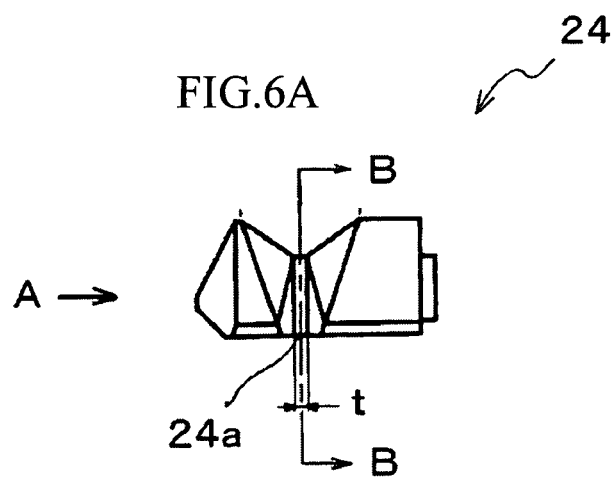
FIGS. 6A-6D are explanation views of a holder 24 of the basket conveying means 22 of the staining apparatus 10.
Figure 6B:
Figure 6C:
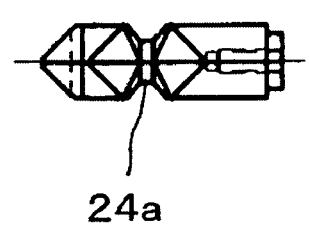

As shown in a front view of FIG. 6A, a side view of FIG. 6B and a plan view of FIG. 6C; in the holder 24 shown in FIG. 6, an end shape seen from a front end of the holder 24 (seen in a direction of an arrow A shown in FIG. 6A) is, as shown in FIG. 6B, formed into a triangular shape, a center part is formed as a thinner part 24a, and the thinner part 24a is formed like a groove. A width t of the thinner part 24a is nearly equal to a thickness of the basket hook 20c, into which the holder 24 will be inserted.

Figure 6D:
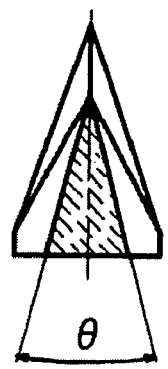

As shown in FIG. 6D which is a sectional view along a line B-B shown in FIG. 6A, a transverse sectional view of the thinner part 24a is formed into a triangular shape, and an apex angle θ is 60° or less (preferably about 30°) and equal to an apex angle θ of the triangular hole 20e of the basket hook 20c.

When the holder 24 shown in FIG. 6 is inserted into the hole 20e of the basket hook 20c shown in FIG. 5 and lifts the basket, the hole 20e of the basket hook 20c is guided toward the groove-shaped thinner part 24a of the holder 24 along a slope face of the holder 24 and engaged with the thinner part 24a. The thickness of the basket hook 20c is nearly equal to the width t of the thinner part 24a of the holder 24, and the apex angle θ of the hole 20e is nearly equal to the apex angle θ of the thinner part 24a. With this structure, the basket hook 20c, whose hole 20e has been engaged with the thinner part 24a of the holder 24, can minimize the swing of the basket 20 while the basket conveying means 22 conveys the basket 20.

A movable tank 26, which can be moved between the inside of the staining apparatus 10 and the inside of the covering apparatus 12, is provided to a covering apparatus 12 side corner of the tank storage section 16 of the staining apparatus 10 shown in FIGS. 1-3. A protective solution for protecting the stained specimen samples is stored in the movable tank 26, and the movable tank 26, in which the baskets 20, in each of which the slide glasses having the specimen samples subjected to desired staining (the slide glasses attached with the stained specimen samples) have been inserted, are soaked in the protective solution, is transferred from an opening section of the casing of the staining apparatus 10 to inside of an opening section of the casing of the covering apparatus 12. The opening section of the casing of the staining apparatus 10 is, as described later, has a width greater than a transverse width of the movable tank 26 so as to adjust a position of the movable tank 26 in the transverse direction.

When the baskets 20, in each of which the slide glasses attached with the stained specimen samples have been stored, are accommodated into the movable tank 26, firstly the holder 24 attached to the elevating member 22c is moved to a position above the tank 18, in which the baskets 20, in each of which the slide glasses attached with the stained specimen samples have been inserted, have been accommodated, by driving the transversal member 22a and the vertical member 22b of the basket conveying means 22.

As shown in FIG. 3, the elevating member 22c is moved downward, the holder is engaged with the hole 20e of the basket hook 20c of the basket 20 accommodated in the tank 18, and then the elevating member 22c is moved upward so as to move the basket 20 to a position above the tank 18.

Next, the transversal member 22a and the vertical member 22b are driven so as to move the basket 20 suspended by the holder 24 to a position above the movable tank 26, and then the elevating member 22c is moved downward so as to insert the basket 20 into the movable tank 26.

As shown in FIG. 2, the staining apparatus 10 shown in FIGS. 1-3 has means for setting a mounting position, at which the basket, in which the slide glasses attached with the stained specimen samples have been stored, is transferred to the movable tank 26 in the staining apparatus 10, to a control section for controlling the basket conveying means 22.

Note that, as shown in FIG. 2, the tank 18, in which the baskets 20 storing the slide glasses attached with the stained specimen samples have been stored, may be manually exchanged as the tank 18, in which the baskets 20 to be transferred to the movable tank 26 have been accommodated, and the baskets 20 storing the slide glasses attached with the stained specimen samples may be directly inserted into the movable tank 26.

Figure 7:
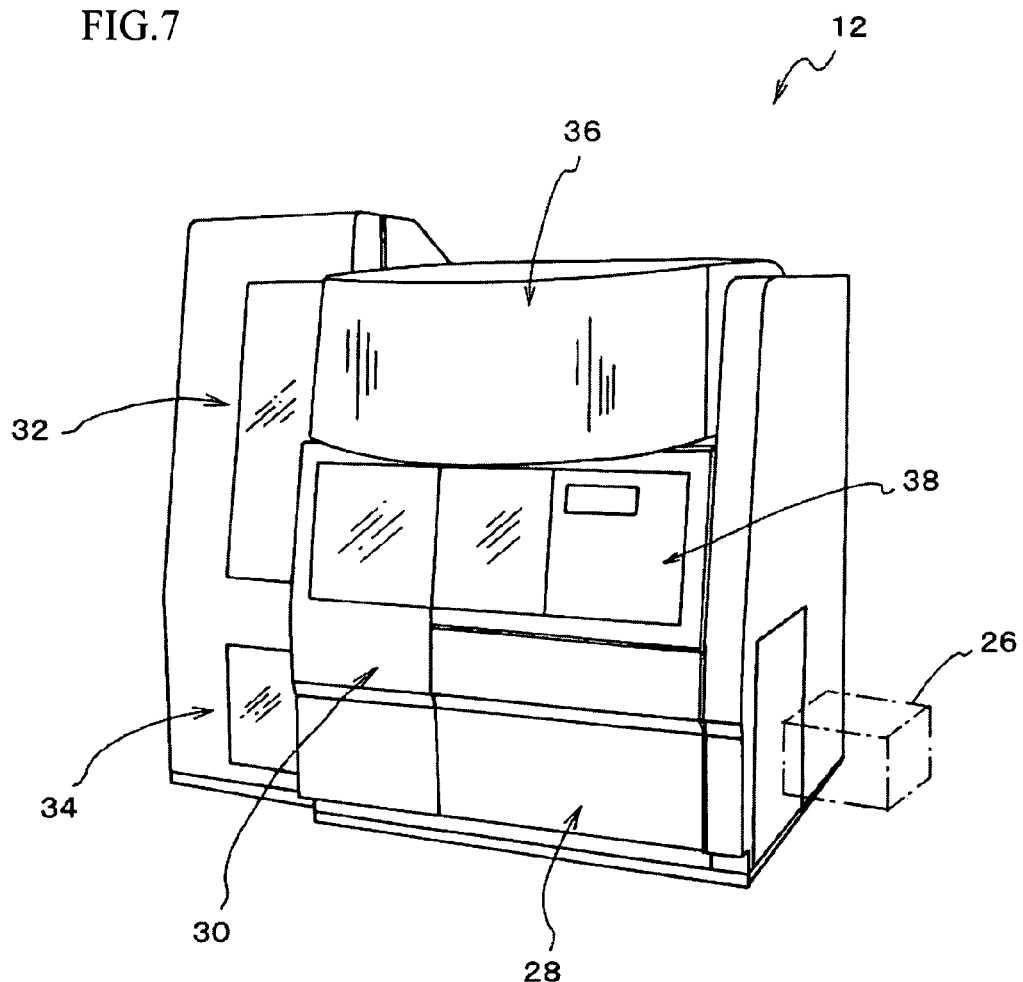
FIG. 7 is a perspective view of the covering apparatus 12 combined with the staining apparatus 10.

The covering apparatus 12 arranged close to the staining apparatus 10 shown in FIGS. 1-3 is shown in FIG. 7.

The covering apparatus 12 shown in FIG. 7 is the covering apparatus 12 capable of covering a cover film, whose one side face is coated with an adhesive, onto the specimen sample on the slide glass.

The movable tank 26 is capable of moving between the inside of the staining apparatus 10 and the inside of the covering apparatus 12 with the baskets 20, in which the slide glasses attached with the stained specimen samples have been stored, being soaked in the protective solution.

The covering apparatus comprises: a movable tank setting section 28, to which the movable tank 26 is transferred and set; a main body part 30 supplying a solvent, e.g., xylene, for solving the adhesive coating the one side face of the cover film to the specimen sample on each of the slide glasses, which is stored in the basket 20 taken out from the movable tank 26 and located at a waiting position, and covering a cover film piece onto the specimen sample; a cover film setting section 32, in which a roll of the cover film, which will be cut to form cover film pieces having a prescribed length, is set; a bottle setting section 34, in which a bottle storing the solvent to be supplied to the specimen sample on each of the slide glasses is set; and a basket accommodating section 36 for accommodating the baskets, each of which store the slide glasses attached with the specimen samples covered with the cover film pieces.

Note that, the covering apparatus 12 shown in FIG. 7 has an operation panel 38 including a start switch, function switches, etc.

Figure 8:
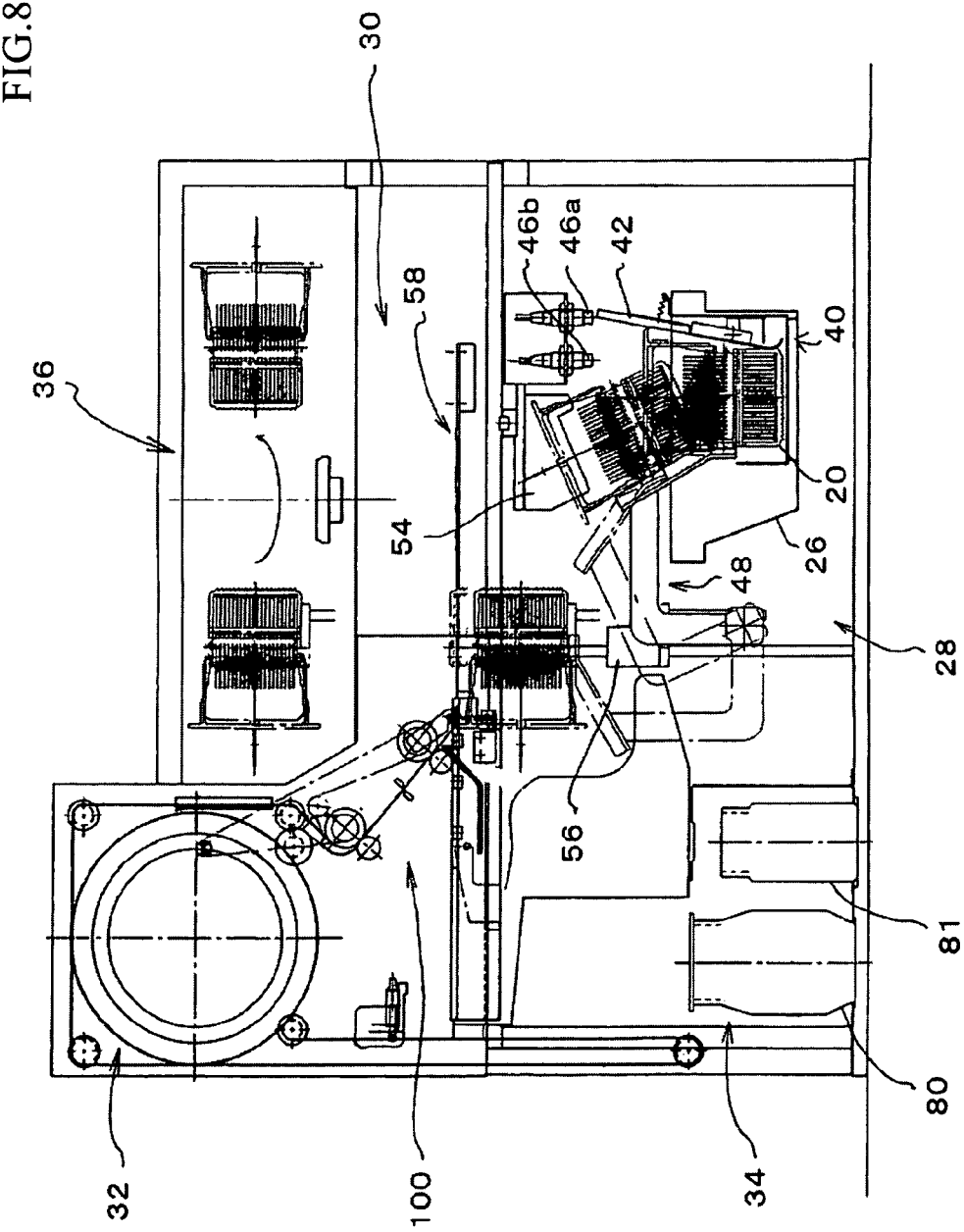
FIG. 8 is a schematic view of an inner structure of the covering apparatus 12 shown in FIG. 7.
Figure 9:
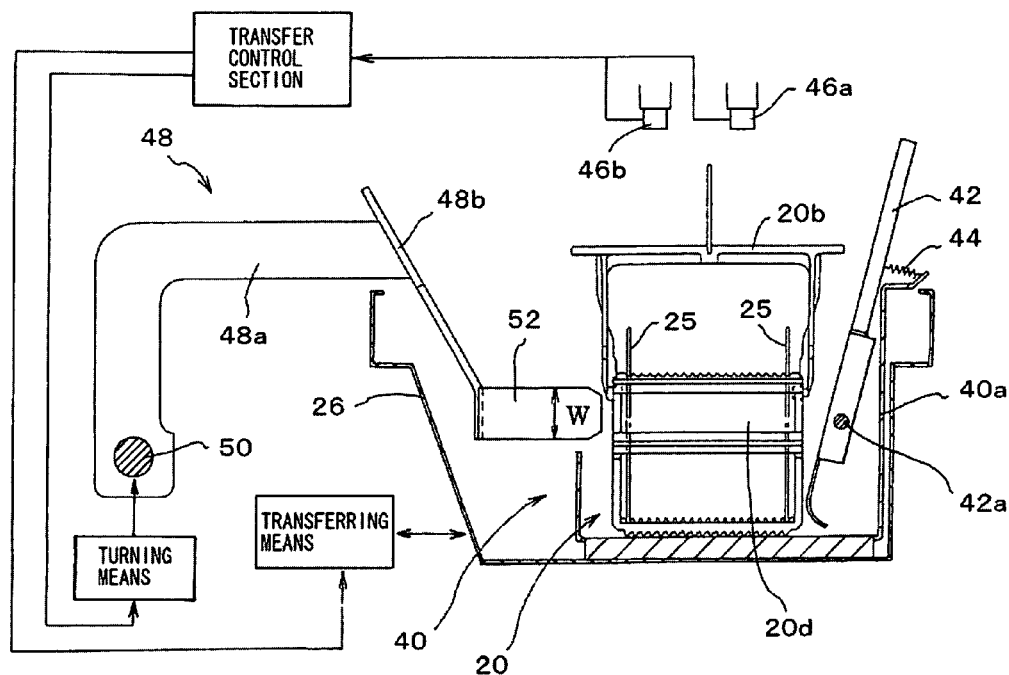
FIG. 9 is a schematic view of a movable tank setting section 28 shown in FIG. 7.

An inner structure of the covering apparatus 12 shown in FIG. 7 is briefly shown in FIG. 8. As shown in FIG. 9, the movable tank 26 located in the movable tank setting section 28 shown in FIG. 8 is moved between the staining apparatus 10 and the covering apparatus 12 by transferring means including a motor, a cylinder unit, etc.

In the movable tank 26, as shown in FIG. 9, a mounting section 40, on which the basket 20 is mounted, is fixed at position close to a side wall of the movable tank 26 located on the one end side, and a strip-shaped member 42 is provided close to a wall 40a of the mounting section 40 and capable of turning about a shaft 42a, which is located at a mid part thereof.

A spring 44, which acts as a biasing member, is provided between the upper end part of the wall 40a and the one end of the strip-shaped member 42 so as to bias the one end of the strip-shaped member 42 toward the wall 40a; the other end of the strip-shaped member 42 is turned away from the wall 40a or turned toward the basket 20 mounted on the mounting section 40 until contacting the basket 20.

Sizes of the baskets 20 are different, and they are based on number of storing the slide glasses. Therefore, sensors 46a and 46b for detecting the one end of the strip-shaped member 42 are provided above the movable tank 26 having the strip-shaped member 42, and they are arranged in the moving direction of the movable tank 26 with a prescribed separation. The sensor 46b is provided on the inner side of the covering apparatus 12 with respect to the sensor 46a.

Figure 10:
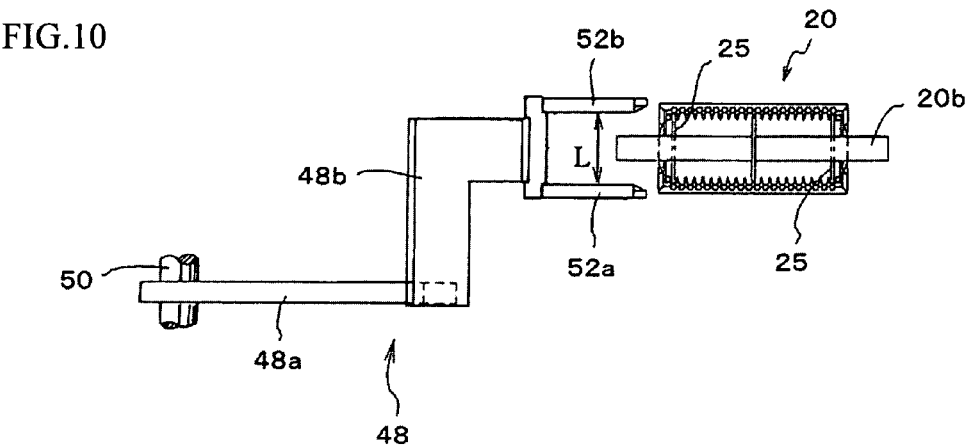
FIG. 10 is an explanation view of the basket 20 accommodated in the movable tank 26 and claw sections 52a and 52b of an arm 48, which are arranged like a U-shape.

As shown in FIGS. 9 and 10, an arm 48, which is constituted by L-shaped members 48a and 48b and capable of turning about a shaft 50 located close to a rear end thereof as shown in FIG. 8, is provided close to movable tank 26. Claw sections 52a and 52b, which constitute a U-shape hand, are provided to a front end the arm 48. As shown in FIG. 10, a space L, in which the basket 20 will be inserted, is formed between the claw sections 52a and 52b; as shown in FIG. 9, the claw sections 52a and 52b having a width W can be inserted in the grooves 20d and 20d of the basket 20.

Means for driving the arm 48, e.g., motor, and the transferring means for transferring the movable tank 26 are controlled by a transfer control section, which receives signals from the sensors 46a and 46b.

After the movable tank 26 is transferred from the staining apparatus 10 to the movable tank setting section 28 shown in FIGS. 7 and 8 by the transferring means, the arm 48 is turned to a position shown in FIG. 9 so as to insert the claw sections 52a and 52b into the grooves 20d and 20d of the basket 20 mounted on the mounting section 40 of the movable tank 26.

Next, the movable tank 26 is moved toward the claw sections 52a and 52b by the transferring means so as to insert the basket 20 into the space between the claw sections 52a and 52b, and only the movement of the basket 20 is stopped.

The basket 20, whose movement has been stopped, presses the other end of the strip-shaped member 42, which moves together with the movable tank 26, in the direction opposite to the biasing direction of the spring 44 by the movement of movable tank 26 moved by the claw sections 52a and 52b of the arm 48. With this action, the strip-shaped member 42 is turned against the elasticity of the spring 44, the one end of the strip-shaped member 42 is moved toward the sensor 46a, and a detection signal of the sensor 46a is sent to the transfer control section.

Upon receiving the detection signal from the sensor 46a, the transfer control section judges that the present basket 20 is bigger than the basket 20 to be detected by the sensor 46b, and restricts the following actions.

Note that, if the both of the sensors 46a and 46b do not detect the one end of the strip-shaped member 42, the transfer control section judges that no baskets 20 exist in the movable tank 26, and stops the following actions.

Figure 11:
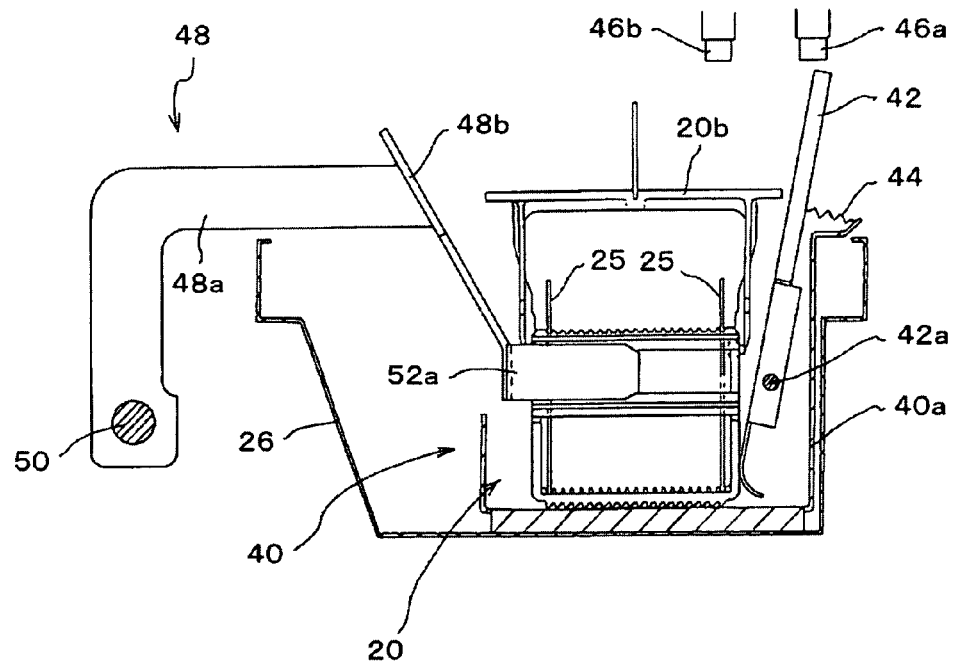
FIG. 11 is an explanation view of the basket 20, which is located between the claw sections 52a and 52b by moving the movable tank 26.

As shown in FIG. 11, when the claw sections 52a and 52b are inserted into the grooves 20d and 20d of the basket 20, which has been mounted on the mounting section 40 of the movable tank 26 and whose handle 20b is turnably attached, and the one end of the strip-shaped member 42 is detected, the transfer control section sends a signal for driving turning means so as to turn the arm 48 as shown in FIG. 8.

By turning the arm 48, the basket 20 held by the claw sections 52a and 52b is taken out from the movable tank 26 and turned until the stored slide glasses 25, 25 . . . are leveled out.

In the turning process, the turning action is once stopped, and the handle pusher 54 is moved in the direction perpendicular to the surface of the drawing sheet of FIG. 8 to turn down the handle 20b of the basket 20. By turning down the handle 20b, the slide glasses 25, 25 . . . stored in the basket 20 can be taken out and/or restored therein without being obstructed by the handle 20b.

The basket 20, whose handle 20b has been turned down, is turned until the stored slide glasses 25, 25 . . . are leveled out, mounted onto an elevating table 56 and lifted until reaching a waiting position.

Figure 12:
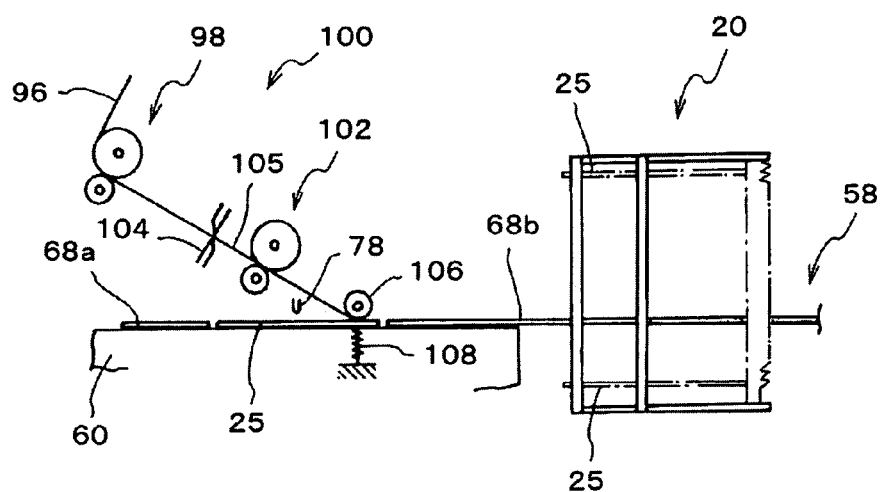
FIG. 12 is a schematic view of a main body section 30 of the covering apparatus 12 shown in FIG. 7.

As shown in FIG. 12, each of the slide glasses 25, 25 . . . stored in the basket 20 located at the waiting position is fed onto a horizontal table 60 by conveying means 58. The slide glass 25 on the horizontal table 60 is moved to a prescribed position in the horizontal table 60 and conveyed from the prescribed position to the basket 20 so as to restore in the same position.

Figure 13:
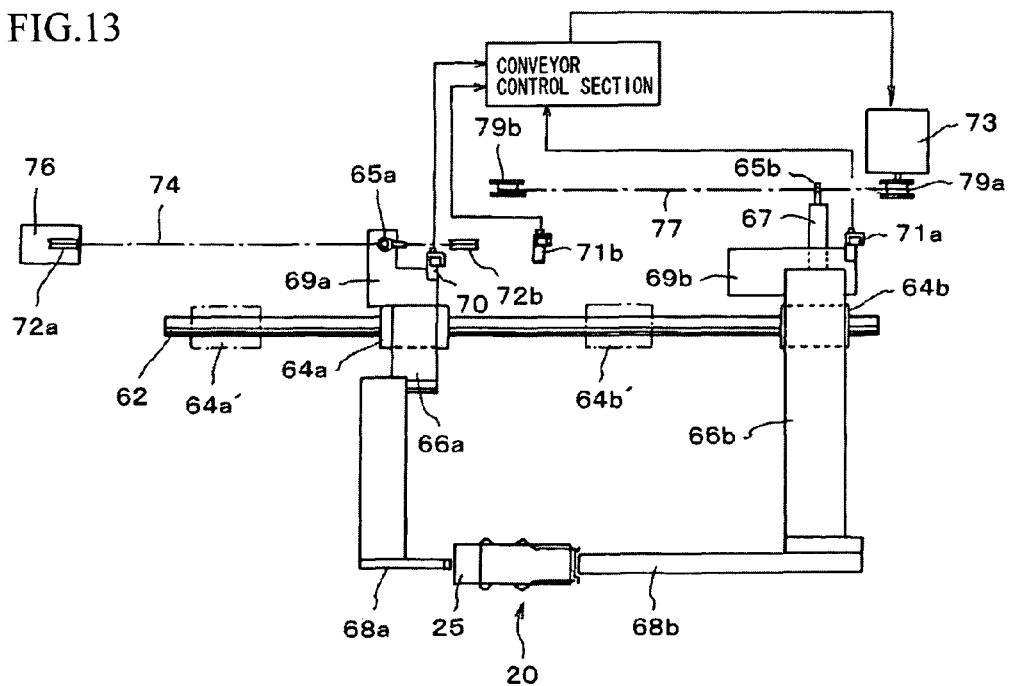
FIG. 13 is a schematic view of conveying means, which is provided to the main body section 30 and which conveys a slide glass 25 stored in the basket 20.

A conveyor shown in FIG. 13 is used as the conveying means 58. In the conveyor shown in FIG. 13, one ends of plate members 66a and 66b are respectively fixed to sliders 64a and 64b, which are slidably attached to a guide member 62, and detection plates 69a and 69b are respectively provided to the one ends thereof. A push ejector 68b, which pushes the slide glass 25 stored in the prescribed position of the basket 20 until reaching the prescribed position in the horizontal table 60, and a return ejector 68a, which returns the slide glass 25 fed at the prescribed position by the push ejector 68b to the initial position in the basket 20, are respectively provided at the other ends of the plate members 66a and 66b.

A belt 77, which is engaged with pulleys 79a and 79b, is fixed to an extended member 67, which is extended from the one end of the plate member 66b, by a fixing member 65b, and the pulley 79a is rotated, in the both direction, by a motor 73 controlled by a conveyor control section. Therefore, the plate member 66b is moved, by the motor 73, along the guide member 62, and the push ejector 68b is also moved along the guide member 62.

On the other hand, the plate member 66a is moved by a wire 74, which is engaged with pulleys 72a and 72b and fixed to a detection plate 69a provided to the one end of the plate member 66a by a fixing member 65a, and a balancer 76 suspended from the end of the wire 74 on the pulley 72a side.

Figure 14:
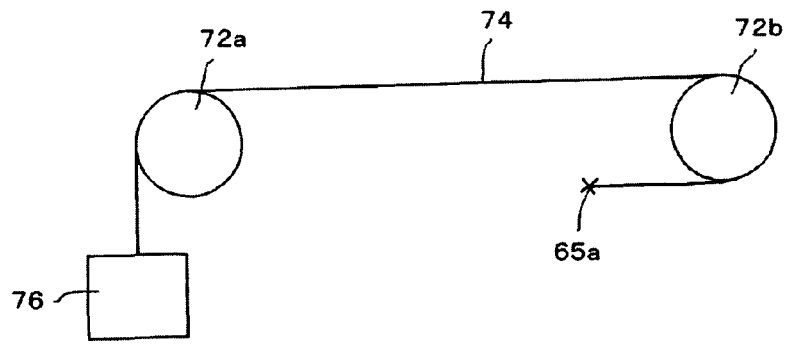
FIG. 14 is an explanation view of a balancer 76 of the conveying means.

As shown in FIG. 14, the balancer 76 is suspended from the pulley 72a side end of the wire 74, which is engaged with the pulleys 72a and 72b, and the pulley 72b side end thereof is fixed to the detection plate 69a by the fixing member 65a. With this structure, the plate member 66a and the return ejector 68a are biased toward the pulley 72b.

Figure 15:
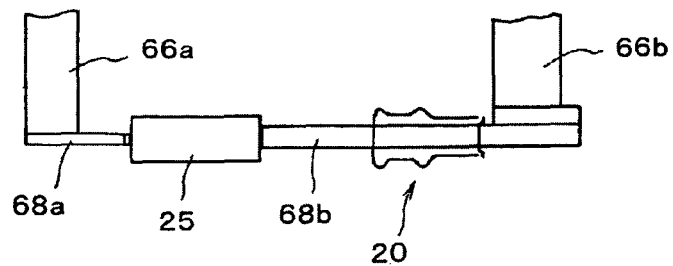
FIG. 15 is an explanation view of the slide glass taken out from the basket 20 by the conveying means.

As shown in FIG. 15, the slide glass 25 stored in the basket 20 is clamped by the return ejector 68a and the push ejector 68b and sent to the horizontal table 60 in the prescribed direction.

The slide glass 25 is clamped by the return ejector 68a and the push ejector 68b and transferred, so weight of the balancer 78 is adjusted so as not to break the slide glass 25 even if the transferring action is locked during the process.

The detection plates 69a and 69b are respectively provided to the one ends of the plate members 66a and 66b shown in FIG. 13, and a sensor 70 detects the detection plate 69a when the front end of the return ejector 68a reaches a position very close to the basket 20 located at the waiting position.

Further, a right sensor 71a and a left sensor 71b for detecting the detection plate 69b are provided, and the right sensor 71a is disposed to detect the detection plate 69b when the front end of the push ejector 68b reaches the position very close to the basket 20 located at the waiting position as shown in FIG. 13. On the other hand, the left sensor 71b is disposed to detect the detection plate 69b when the sliders 64a and 64b reach positions 64a' and 64b' shown in FIG. 13. When the left sensor 71b detects the detection plate 69b, the push ejector 68b pierces through the basket 20 and reaches the prescribed position in the horizontal table 60 as shown in FIG. 15.

Detection signals of the sensors 70, 71a and 71b are sent to the conveyor control section, and a signal for driving or stopping the motor 73 is sent from the conveyor control section.

When the slide glass 25 is taken out from the basket 20 located at the waiting position and fed onto the horizontal table 60, the conveyor control section rotates the motor 73 in the normal direction so as to make the front end of the push ejector 68b contact one end of the slide glass 25 stored in the basket 20 and push out the slide glass 25 from the basket 20 toward the horizontal table 60.

The slide glass 25, which has been pushed out from the basket 20 by the push ejector 68b, is moved away from the basket 20 against a force applied from the balancer 76, which is generated by contact between the other end of the slide glass and the front end of the return ejector 68a. At that time, the plate member 66b is moved toward the left sensor 71b, so that the right sensor 71a, which has detected the detection plate 69b, sends an OFF signal to the conveyor control section; the detection plate 69a of the plate member 66a is moved, so that the sensor 70, which has detected the detection plate 69a, sends an OFF signal to the conveyor control section.

When the detection plate 69b of the plate member 66b is moved and detected by the left sensor 71b, the slide glass 25 transferred by the push ejector 68b is located at the prescribed position as shown in FIG. 12. Upon receiving the signal of detecting the detection plate 69b from the left sensor 71b, the conveyor control section sends a signal for stopping the motor 73 and a signal for rotating the same in the reverse direction.

With this action, the push ejector 68b is moved toward the basket 20 with the front end contacted the slide glass 25 pushed by the return ejector 68a.

The push ejector 68b passes through the basket 20, and the slide glass 25 is restored in the initial position of the basket 20, then the conveyor control section receives the signal of detecting the detection plate 69b from the right sensor 71a and sends a signal for stopping the reverse rotation of the motor 73.

At that time, in case that no slide glass 25 is stored in the prescribed position of the basket 20 located at the waiting position, the detection plate 69a of the plate member 66a can be detected by the sensor 70 even if the detection plate 69b of the plate member 66b is not detected by the right sensor 71a. Therefore, even if the right sensor 71a sends the OFF signal, the conveyor control section judges that no slide glass 25 is stored in the prescribed position of the basket 20 as far as the sensor 70 sends the ON signal and tries to convey the next slide glass 25 stored in the basket 20.

The slide glass 25 conveyed from the prescribed position of the basket 20 to the horizontal table 60 by the conveying means 58 is conveyed to the prescribed position of the horizontal table 60, and a mounting medium is dropped onto the stained specimen sample on the slide glass 25 from a metallic nozzle 78 and a cover film piece is covered thereonto as shown in FIG. 12 while the slide glass is stayed at the prescribed position and restored in the initial position of the basket 20 located at the waiting position.

Figure 16:
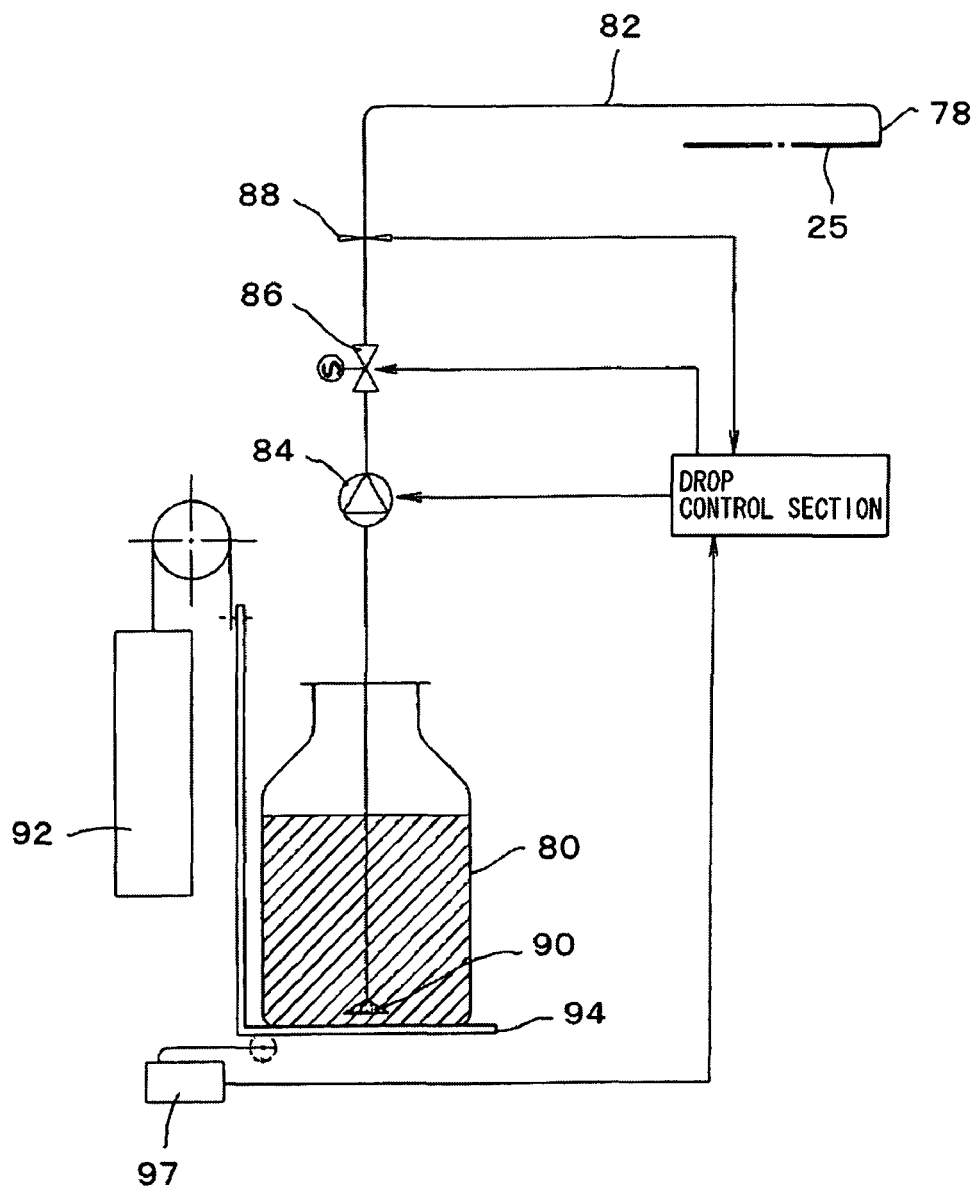
FIG. 16 is an explanation view of means for dropping a mounting medium onto the slide glass 25 conveyed by the conveying means.

Dropping means shown in FIG. 16 is connected to the metallic nozzle 78. The dropping means includes a transparent tube 82 for feeding the mounting medium, which is stored in a storing bottle 80 mounted on the bottle setting section 34 of the covering apparatus 12 shown in FIG. 8, and a pump 84, an electromagnetic valve 86 and a bubble sensor 88 are provided to the tube 82 in that order from the bottle 80 side.

The pump 84 and the electromagnetic valve 86 are controlled by a drop control section, and a bubble detection signal is sent to the drop control section when the bubble sensor 88 detects a bubble of bubbles in the tube 82.

A filter 90 is attached to the front end part of the tube 82, which is inserted in the bottle 80, so as to prevent dusts in the bottle 80 from sucking into the tube 82 when the bottle 80 is exchanged.

The bottle 80 is mounted on a table 94, to which an upward force is applied by a weight member 92 whose weight is equal to a total weight of a tare of the bottle 80 and the mounting medium stored in the bottle 80. The table 94 is moved upward and downward by an amount of the mounting medium stored in the bottle 80, so the amount of the mounting medium stored in the bottle can be known by measuring the position of the table 94. Therefore, when the amount of the mounting medium is less than a prescribed amount and the table 94 is moved upward until reaching a prescribed position, a sensor 97 sends a detection signal to the drop control section. Upon receiving the signal from the sensor 97, the drop control section sends a hold signal, which indicates to stop taking out the new basket 20 from the movable tank 26, to the transfer control section (see FIG. 9).

When the bottle 80 is exchanged, air is sometimes sucked into the tube 82 and a bubble or bubbles are formed in the tube 82. The bubbles in the tube 82 vary an amount of the mounting medium dropped onto the slide glasses 25. When the drop control section receives the bubble detection signal from the bubble sensor 88, the drop control section drives the pump 84 so as to fully discharge the mounting medium in the tube 82 from the nozzle 78 and sends a signal for opening the electromagnetic valve 86. The discharged mounting medium is stored into a waste holdup bottle 81 (see FIG. 8) mounted on the bottle setting section 34. When the mounting medium is fully discharged from the tube 82, the drop control section stops the pump 84 and sends a signal for closing the electromagnetic valve 86.

Preferably, in the dropping means shown in FIG. 16, a length between the bubble sensor 88 and the nozzle 78 is designed to secure the enough amount of the mounting medium, which can be dropped onto the maximum number of the slide glasses 25 stored in the basket 20 located at the waiting position. By securing the enough amount of the mounting medium, which can be dropped onto the maximum number of the slide glasses 25 stored in the basket 20 located at the waiting position, an undesired case, in which the mounting medium cannot be dropped onto a part of the slide glasses 25 stored in the basket 20 located at the waiting position, can be avoidable.

Note that, by providing the bubble sensor 88, the bubble sensor 88 sends the bubble detection signal when the mounting medium in the bottle 80 is reduced and a bubble or bubbles are formed in the tube 82, so a time for exchanging the bottle 80 can be known without providing the table 94, the weight member 92 and the sensor 97.

The cover film pieces are pressed and pasted onto the slide glasses 25, on each of which the mounting medium has been dropped by the dropping means shown in FIG. 16, by covering means 100 shown in FIG. 12.

The covering means 100 feeds a long cover film 96 toward the slide glass 25 by a pair of feeding rollers 98 and a pair of cover rollers 102 as shown in FIG. 12, and the cover film 96 is cut by a cutter 104 located between the feeding rollers 98 and the cover rollers 102 so as to form the cover film piece 105 having a prescribed length as shown in FIG. 12. The cover film piece 105 is pressed onto the slide glass 25 by a covering roller 106 so as to paste thereon. A shaft of the covering roller 106 is biased toward the horizontal table 60 by elasticity of biasing means, e.g., spring 108, and the cover film piece 105 can be pressed onto the slide glass 25 with a fixed force.

In the covering means 100 shown in FIG. 12, the length of the cover film piece 105 is set by the operation panel 38 (see FIG. 7), and the cutter 104, which acts as cutting means, cuts at a prescribed timing from the start of feeding the cover film 96 by the feeding rollers 98. Therefore, if the timing of actuating the cutter 104 from the start of feeding the cover film 96 by the feeding rollers 98 is made earlier, the length of the cover film piece 105 is made shorter.

A point of starting to paste the cover film piece 105 onto the slide glass 25 can be adjusted by timing of starting to drive the cover rollers 102. Namely, if the cover rollers 102 are driven earlier with respect to the slide glass 25 conveyed on the horizontal table 60, the cover film piece 105 can be pasted closer to the one end of the slide glass 25. Therefore, the point of starting to paste the cover film piece 105 from the one end of the slide glass 25 is set by the operation panel 38, so that the cover film piece 105 can be pasted at a prescribed position.

In the covering means 100 shown in FIG. 12, the slide glass 25, which has been stored in the prescribed position of the basket 20 located at the waiting position, is clamped by the return ejector 68a and the push ejector 68b and pushed out toward the horizontal table 60 by the push ejector 68b, the slide glass 25 is moved away from the basket 20 by the push ejector 68b until passing the nozzle 78, then the push ejector 68b stops the movement of the slide glass 25.

Next, the slide glass 25 is moved toward the basket 20, by the return ejector 68a, until the nozzle 78 reaches a position which is a prescribed distance away from the one end of the slide glass 25, and the mounting medium is dropped from the nozzle 78, then the feeding rollers 98 and the cover rollers 102 are driven, the cutter 104 is actuated at the prescribed timing and a front end of the cover film piece 105 having the prescribed length is fed to the prescribed position of the slide glass 25. The cover film piece 105, which has been fed to the prescribed position of the slide glass 25, is pressed and pasted onto the slide glass 25 by the covering roller 106.

When the slide glass 25 is moved toward the basket 20 by the return ejector 68a, a speed of returning the slide glass 25 can be adjusted by adjusting a return speed of the push ejector 68b contacting the slide glass 25 or a rotational speed of the motor 73 rotated in the reverse direction.

The long cover film 96 shown in FIG. 12 is fed from cover film feeding means of the cover film setting section 32 shown in FIG. 7.

Figure 17:
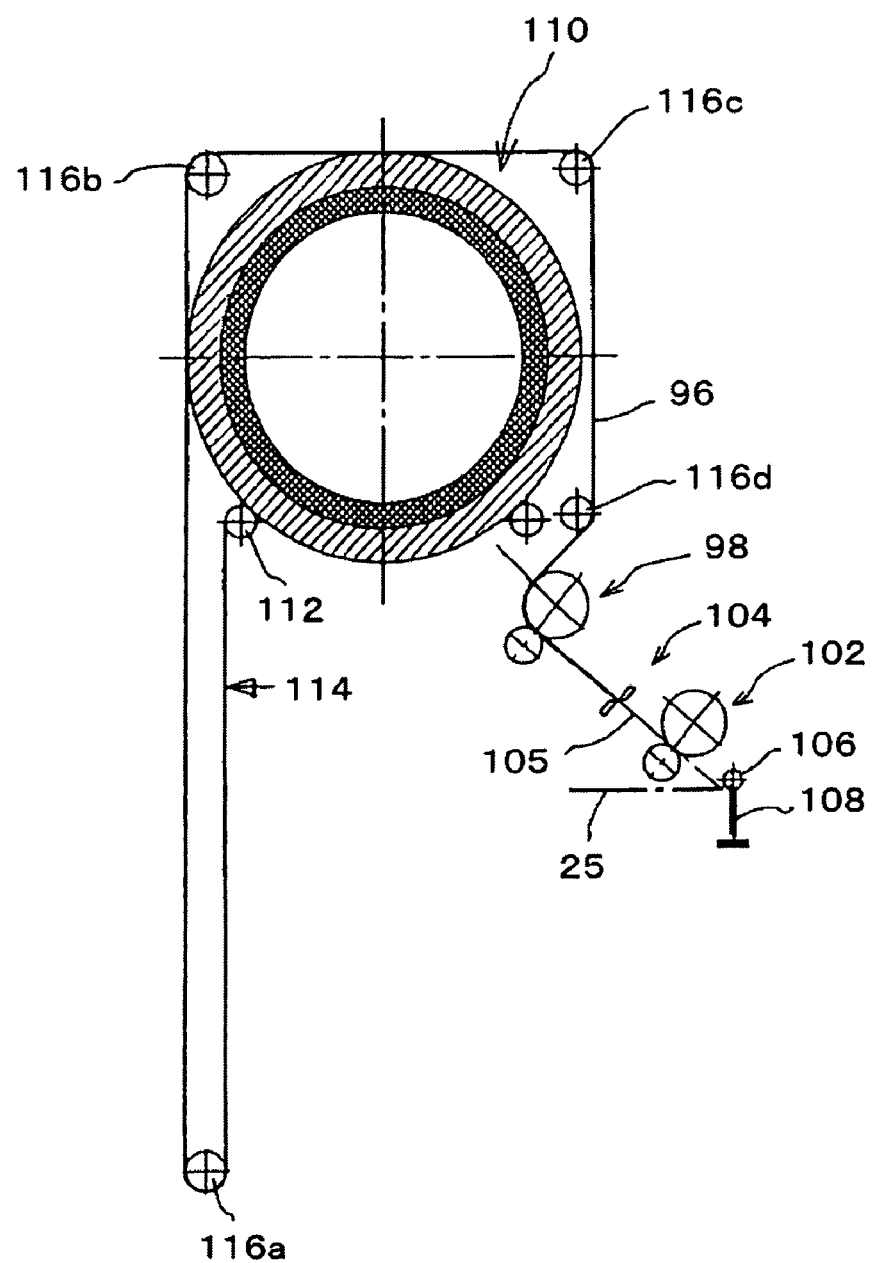
FIG. 17 is a schematic view of an example of a cover film setting section 32 of the covering apparatus 12.

In the cover film feeding means, the cover film 96 extended from a cover film roll 110, on which the cover film 96 is wound, is extended from an extending roller 112 to the feeding rollers 98 via a sensor 114 for detecting a termination end of the cover film 96 extended from the extending roller 112 and guide rollers 116a-116d provided around the cover film roll 110 as shown in FIG. 17.

A length of the cover film 96 between the sensor 114 and the feeding rollers 98 is designed to paste the cover film pieces 105 onto the maximum number of the slide glasses 25 stored in the basket 20 located at the waiting position. By the cover film length securing means including the guide rollers 116a-116d provided around the cover film roll 110, the cover film pieces 105 can be pasted onto all of the slide glasses 25 stored in the basket 20 located at the waiting position even if the sensor 114 detects the termination end of the cover film 96 while processing the slide glasses 25 stored in the basket 20 located at the waiting position.

The detection signal of the sensor 114 is sent to the conveyor control section (see FIG. 9), and no basket 20 is newly taken out from the movable tank 26 and transferred from the staining apparatus 10 to the movable tank 26.

The slide glass 25, on which the cover film piece 105 is pasted, is restored in the initial position of the basket 20 located at the waiting position. After the cover film pieces 105 are pasted onto all of the slide glasses 25 stored in the basket 20, the basket 20 is accommodated in the basket accommodating section 36 (see FIG. 7) located above the waiting position by the elevating table 56. In the basket accommodating section 36, basket accommodating members are rotatably provided so as to accommodate a plurality of the baskets 20.

As described above, the basket 20 accommodated in the movable tank 26 stores the slide glasses 25, on which the cover film pieces 105 have been pasted, and is accommodated in the basket accommodating section 36, so the basket 20 is moved in one direction only, i.e., from the staining apparatus 10 to the covering apparatus 12. Therefore, only the movable tank 26 is returned to the staining apparatus 10, so the transferring means for moving the movable tank 26 can be simplified.

Figure 18:
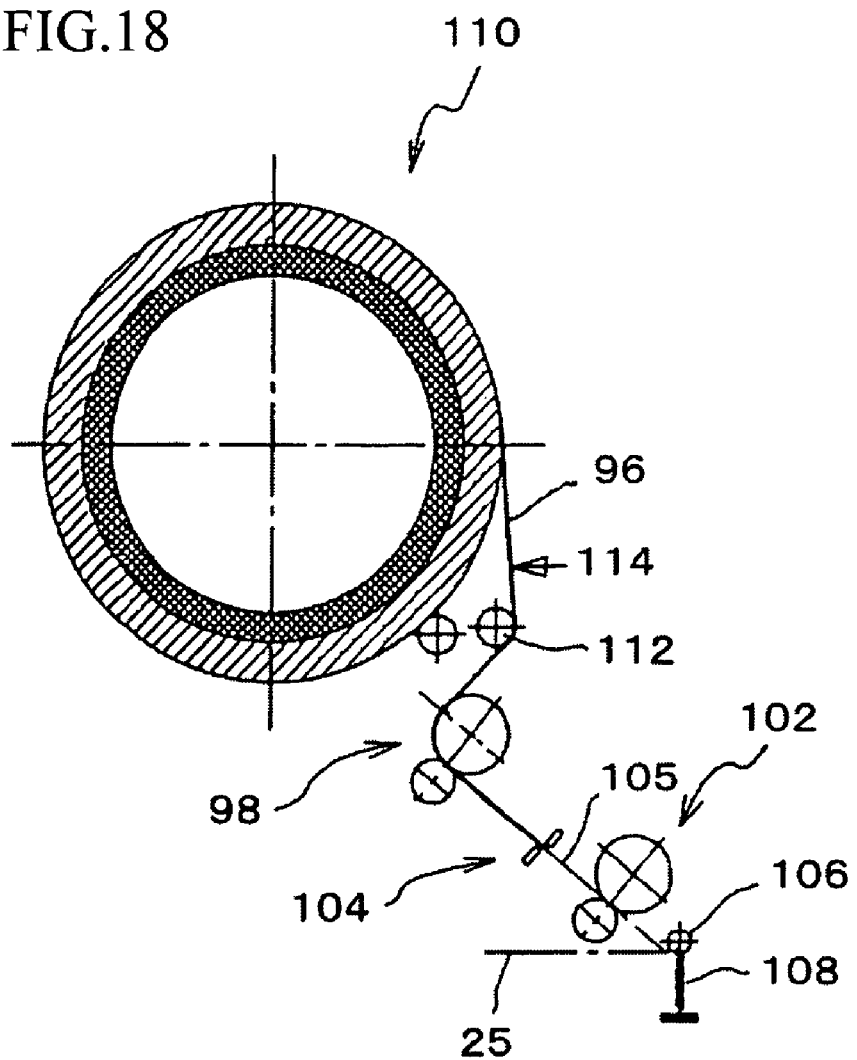
FIG. 18 is a schematic view of another example of the cover film setting section 32.

In the cover film length securing means shown in FIG. 17, the guide rollers 116a-116d provided around the cover film roll 110 extend the cover film 96 so as to secure the length of the extended cover film 96, so enough space must be secured in the covering apparatus 12. Therefore, a prescribed position of the cover film 96, which is separated a prescribed distance away from the termination end thereof so as to paste the cover film pieces 105 onto all of the slide glasses 25 stored in the basket 20 located at the waiting position, is previously marked, and the mark may be detected by the sensor 114, which is provided immediately before the feeding rollers 98 as shown in FIG. 18.

Further, the size of the movable tank 26 may be designed to accommodate the baskets 20, 20 . . . in parallel. In this case, a plurality of the strip-shaped members 42 must be provided in parallel.

When the staining apparatus 10 shown in FIGS. 2-6 and the covering apparatus 12 shown in FIGS. 7-18 are combined, an actual distance between the opening section of the casing of the covering apparatus 12, through which the movable tank 26 enters and goes out, and the opening section of the casing of the staining apparatus 10 (a distance in the moving direction of the movable tank 26) will be slightly different from a designed distance, and an actual distance of transferring the movable tank 26, which is transferred by the transferring means of the covering apparatus 12, will be different. These problems can be easily solved by changing the mounting position, at which the basket is transferred to the movable tank 26 in the staining apparatus 10, according to the transferring distance of the transferring means in the covering apparatus 12. The changed mounting position of the movable tank 26 in the staining apparatus 10 is inputted to the control section shown in FIG. 2, which controls the basket conveying means 22, by the setting means.

Further, the above described problems can be solved by changing the distance of transferring the movable tank 26, which is transferred by the transferring means of the covering apparatus 12, without changing the mounting position, at which the basket is transferred to the movable tank 26 in the staining apparatus 10. The change of the transferring distance of the transferring means can be performed by inputting the changed distance to setting means of the transfer control section of the covering apparatus 12.

Even if the center of the opening section of the casing of the covering apparatus 12, through which the movable tank 26 enters and goes out, and the center of the opening section of the casing of the staining apparatus 10 are slightly shifted, the problem can be easily solved by changing the mounting position, at which the basket is transferred to the movable tank 26 in the staining apparatus, because a width of the opening section of the staining apparatus 10 is wider than a transverse width of the movable tank 26. In this case too, the changed mounting position of the movable tank 26 in the staining apparatus 10 is inputted to the control section, which controls the basket conveying means 22, by the setting means.

As described above, the staining apparatus 10 shown in FIGS. 2-6 and the covering apparatus 12 shown in FIGS. 7-18 can be easily combined without performing severe positioning control.

Setting the mounting position, at which the basket is transferred to the movable tank 26 in the staining apparatus 10, may be manually inputted by a keyboard, and the mounting position may be detected by inserting the basket into the movable tank 26 mounted at the prescribed position in the staining apparatus 10.

The mounting position, at which the basket is transferred to the movable tank 26 in the staining apparatus 10, may be detected by a sensor, etc.

The covering apparatus 12 shown in FIGS. 7-18 pastes the cover film pieces 105 having the prescribed length onto the stained specimen samples on the slide glasses 25, and the covering apparatus 12 may paste cover glasses onto the stained specimen samples on the slide glasses 25 instead of the cover film pieces 105.

Figure 19:
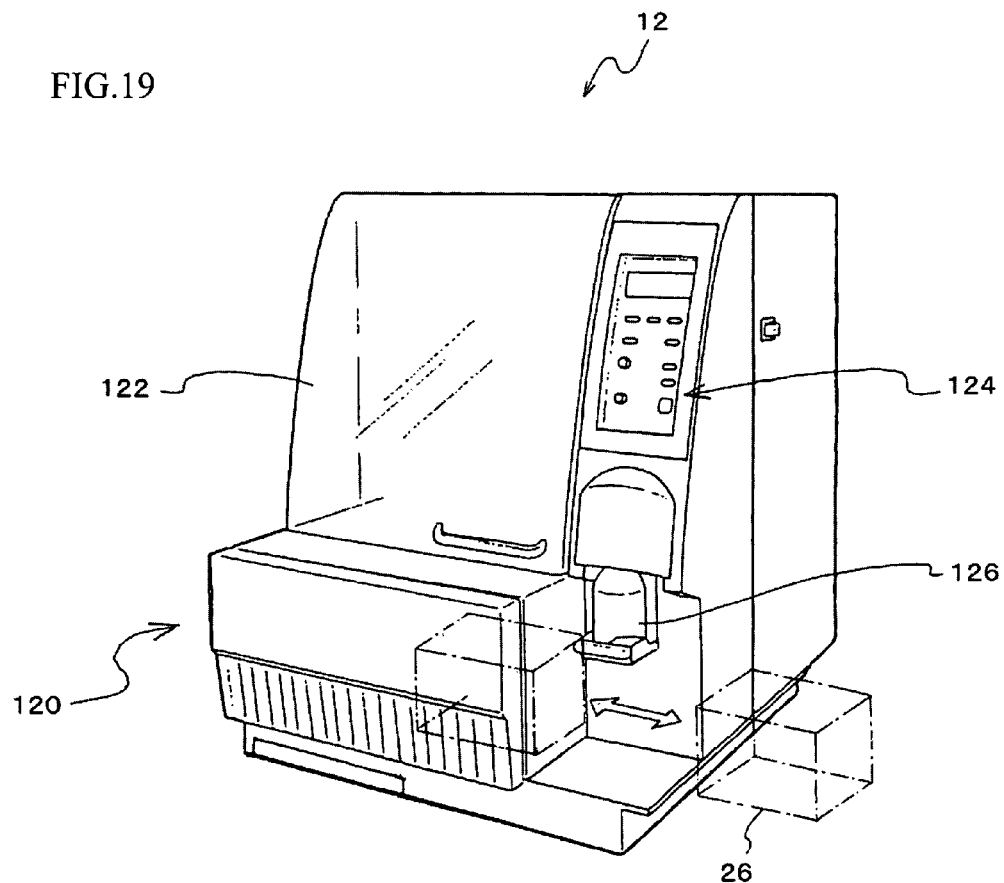
FIG. 19 is a perspective view of another covering apparatus 12, which can be used instead of the covering apparatus 12 shown in FIGS. 7-18.

The covering apparatus 12 shown in FIG. 19, which is disclosed in Japanese Patent Kokai Gazette No. 2001-27731, may be used as the covering apparatus 12 capable of covering cover glasses onto slide glasses.

In the covering apparatus 12 shown in FIG. 19, a transparent cover 122 is capable of opening and closing a main body section 120, and an operation panel 124 is provided to the main body section 120. Further, a container 126 storing a mounting medium is inserted in the main body section 120.

Figure 20:
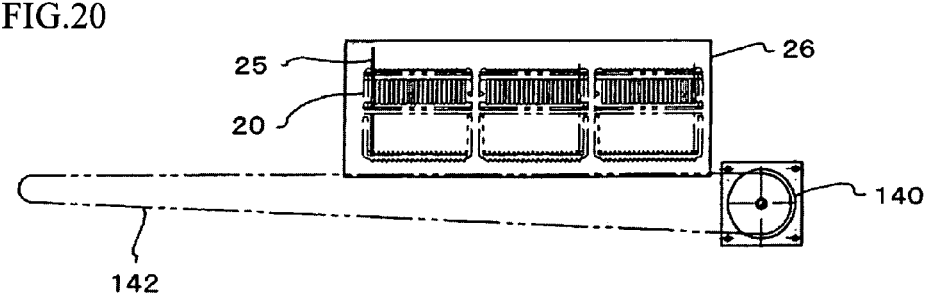
FIG. 20 is an explanation view of means for transferring the movable tank 26 of the covering apparatus 12 shown in FIG. 19.

The movable tank 26 is transferred between the main body section 120 and the staining apparatus 10. As shown in FIG. 20, the transferring means for transferring the movable tank 26 is constituted by a motor 140 provided in the main body section 120 and a wire 142 driven by the motor 140, and the front end of the wire 142 is extended until reaching the inside of the staining apparatus 10.

In case that the slide glass attached with the stained specimen sample to be urgently pasted exists in the covering apparatus 12 shown in FIGS. 7-18 as shown in FIG. 2, the movable tank 26, in which the basket 20 storing the slide glass attached with the stained specimen sample is inserted, may be manually fed as shown in FIG. 2.

By the way, in the staining/covering system shown in FIGS. 1-20, the casings of the staining apparatus 10 and the covering apparatus 12 are arranged to partially contact each other at least, but a gap may be formed between the casings of the staining apparatus 10 and the covering apparatus 12. By forming the gap, many types of staining apparatuses 10 can be combined with the covering apparatus 12 shown in FIGS. 7-18.

By forming the gap between the covering apparatus 12 shown in FIGS. 7-18 and the staining apparatus 10, the system can be highly optionally designed. For example, a plurality of the staining apparatuses can be combined with the covering apparatus 12 shown in FIGS. 7-18 due to high covering performance.

Further, an installation layout of the covering apparatus 12 shown in FIGS. 7-18 and the staining apparatus 10 may be optionally designed.

In case of combining with a plurality of the staining apparatuses or changing the installation layout of the covering apparatus 12 and the staining apparatus 10, the distance between the opening section of the casing of the covering apparatus 12, through which the movable tank 26 enters and goes out, and the opening section of the casing of the staining apparatus 10 will be easily changed or the centers of the both casings will be easily shifted. The problems can be solved by changing the mounting position, at which the basket is transferred to the movable tank 26 in the staining apparatus 10, and inputting the changed mounting position of the movable tank 26 to the control section shown in FIG. 2, which controls the basket conveying means 22, by the setting means.

In case that the transferring means of the covering apparatus 12, which transfers the movable tank 26, has means for adjusting the position according to the mounting position of the movable tank 26 in the staining apparatus 10, and means for setting the mounting position of the movable tank 26 in the staining apparatus 10 may be provided to a control section for controlling the adjusting means so as to change the position of the transferring means of the covering apparatus 12 according to the mounting position of the movable tank 26 in the staining apparatus 10.

Note that, the protective solution for protecting the stained specimen samples is stored in the movable tank 26, which is moved between the staining apparatus 10 and the covering apparatus 12, but, in case that the covering apparatus 12 pastes the cover film piece of the cover glass immediately after the staining apparatus 10 stains the specimen sample on the slide glass, no protective solution may be stored in the movable tank 26.

What is claimed is:

1. A staining/covering system comprising:
   a staining apparatus for staining a specimen sample sliced and pasted to a glass slide; and
   a covering apparatus being arranged in close proximity to said staining apparatus and covering a cover film or a cover glass onto the specimen sample of the glass slide subjected to desired staining in said staining apparatus,
   transferring means for transferring a movable tank from inside of said staining apparatus to inside of said covering apparatus, said transferring means being provided in said covering apparatus,
   said staining apparatus includes a basket wherein one or a plurality of glass slides having specimen samples are inserted perpendicular to a bottom part;
   a plurality of stationary tanks storing staining liquid or cleaning liquid, in which the basket is soaked so as to stain or clean the specimen sample or samples of said plurality of glass slides;
   said movable tank being reciprocally moved between said staining apparatus and said covering apparatus by said transferring means; and
   means for conveying the basket to at least one of said plurality of stationary tanks and conveying the basket, in which the glass slide or glass slides having the specimen sample or samples stained or cleaned are stored, to said movable tank that is located at a predetermined position in said staining apparatus by said transferring means.

2. The staining/covering system according to claim 1, wherein the transferring means transfers the basket, in which the glass slide is stored, from said staining apparatus to said covering apparatus, and
   said staining apparatus or said covering apparatus has means for setting a mounting position in said staining apparatus, at which the basket to be transferred to said covering apparatus is mounted, to a control section for controlling means for conveying the slide glass, which is provided in said staining apparatus, or a control section for controlling the transferring means of said covering apparatus.

3. The staining/covering system according to claim 1, wherein casings of said staining apparatus and said covering apparatus are arranged to partially contact each other at least.

4. The staining/covering system according to claim 1, wherein the transferring means transfers the glass slide having the specimen sample stained in said staining apparatus from said staining apparatus to said covering apparatus with the specimen sample being soaked in a protective solution.

5. The staining/covering system according to claim 1, wherein a protective solution for protecting the specimen sample is stored in the movable tank.

6. A staining/covering system comprising:
   a staining apparatus for staining a specimen sample sliced and pasted to a glass slide;
   a covering apparatus being arranged in close proximity to said staining apparatus and covering a cover film or a cover glass onto the specimen sample of the glass slide subjected to desired staining in said staining apparatus,
   transferring means for transferring a movable tank from inside of said staining apparatus to inside of said covering apparatus, said transferring means being provided in said covering apparatus said staining apparatus includes a basket having a plurality of glass slides,
   said staining apparatus includes a plurality of stationary tanks storing staining liquid or cleaning liquid, in which the basket is soaked so as to stain or clean the specimen sample or samples of said plurality of glass slides; said movable tank being reciprocally moved between said staining apparatus and said covering apparatus by said transferring means;
   said transferring means further transfers said movable tank to a covering position in said covering apparatus, at which the cover film or the cover glass is pasted on at least one of said plurality of glass slides and then returned into said basket;
   means for dropping a solvent or a mounting medium onto at least one of said plurality of slides before at least one of said plurality of glass slides reaches said covering position; and
   means for pressing the cover film or the cover glass onto the solvent or the mounting medium on the specimen sample so as to paste the cover film or the cover glass thereon.

* * * * *